(12) United States Patent
Bergman et al.

(10) Patent No.: US 12,207,951 B2
(45) Date of Patent: Jan. 28, 2025

(54) SYSTEMS AND METHODS FOR DETECTION OF POTENTIAL HEALTH ISSUES

(71) Applicant: Fresenius Medical Care Holdings, Inc., Waltham, MA (US)

(72) Inventors: Eric Bergman, Newton, MA (US); Jonathan Leclerc, Northborough, MA (US); David Yuds, Hudson, NH (US); Maria Tamayo-Coffey, Pleasanton, CA (US); Jessica Steuber, Berlin, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 19 days.

(21) Appl. No.: 17/832,405

(22) Filed: Jun. 3, 2022

(65) Prior Publication Data

US 2022/0296175 A1     Sep. 22, 2022

Related U.S. Application Data

(63) Continuation of application No. 16/534,319, filed on Aug. 7, 2019, now Pat. No. 11,350,887.

(51) Int. Cl.
*A61B 5/00* (2006.01)
*A61B 3/12* (2006.01)
(Continued)

(52) U.S. Cl.
CPC .......... *A61B 5/7275* (2013.01); *A61B 5/0205* (2013.01); *A61B 5/746* (2013.01);
(Continued)

(58) Field of Classification Search
CPC ..... A61B 5/7275; A61B 5/0205; A61B 5/746; A61B 3/12; A61B 5/021; A61B 5/201; G01G 19/50; G16H 50/00–50/80
See application file for complete search history.

(56) References Cited

U.S. PATENT DOCUMENTS 9,828,637 B2    11/2017   Genovese et al.
10,978,176 B2    4/2021    Cha et al.
(Continued)

FOREIGN PATENT DOCUMENTS

CN    108573753     9/2018
DE    19920233      12/2000
(Continued)

OTHER PUBLICATIONS

Vadalà, Maria, et al. "Retinal and choroidal vasculature changes associated with chronic kidney disease." Graefe's Archive for Clinical and Experimental Ophthalmology 257 (2019): 1687-1698. DOI:10.1007/s00417-019-04358-3 (Year: 2019).*
(Continued)

*Primary Examiner* — Jonathan T Kuo
(74) *Attorney, Agent, or Firm* — Fish & Richardson P.C.

(57) ABSTRACT

A device for detecting potential health issues includes a retinal scanner configured to capture retinal data of the user, a blood pressure sensor configured to capture blood pressure data of the user, an alert module configured to alert the user of a potential health risk, and at least one processor communicatively coupled to the retinal scanner, the blood pressure sensor, and the alert module.

20 Claims, 4 Drawing Sheets

(51) Int. Cl.
- *A61B 5/0205* (2006.01)
- *A61B 5/021* (2006.01)
- *A61B 5/20* (2006.01)
- *G01G 19/50* (2006.01)
- *G16H 50/30* (2018.01)

(52) U.S. Cl.
CPC ............. *G01G 19/50* (2013.01); *G16H 50/30* (2018.01); *A61B 3/12* (2013.01); *A61B 5/021* (2013.01); *A61B 5/201* (2013.01)

(56) References Cited

U.S. PATENT DOCUMENTS

| | | | |
|---|---|---|---|
| 11,350,887 B2* | 6/2022 | Bergman | A61B 5/746 |
| 2005/0261558 A1 | 11/2005 | Eaton et al. | |
| 2005/0272101 A1 | 12/2005 | Devarajan et al. | |
| 2008/0292151 A1 | 11/2008 | Kurtz et al. | |
| 2010/0190164 A1 | 7/2010 | Tammen et al. | |
| 2011/0033942 A1 | 2/2011 | Hess et al. | |
| 2011/0257891 A1 | 10/2011 | Akonur et al. | |
| 2012/0034240 A1 | 2/2012 | Kas et al. | |
| 2012/0077690 A1 | 3/2012 | Singbartl et al. | |
| 2013/0079244 A1 | 3/2013 | Genovese et al. | |
| 2013/0143806 A1 | 6/2013 | Nelsestuen | |
| 2013/0323751 A1 | 12/2013 | Singbartl et al. | |
| 2013/0330829 A1 | 12/2013 | Demirjian | |
| 2014/0354949 A1 | 12/2014 | Bakar et al. | |
| 2014/0377777 A1 | 12/2014 | Anderberg et al. | |
| 2015/0056641 A1 | 2/2015 | Anderberg et al. | |
| 2015/0241415 A1 | 8/2015 | Anderberg et al. | |
| 2016/0342764 A1* | 11/2016 | Hermida Domingez | G16H 70/60 |
| 2016/0357923 A1 | 12/2016 | Dong et al. | |
| 2017/0007126 A1 | 1/2017 | Shahar | |
| 2017/0046487 A1 | 2/2017 | Tran | |
| 2017/0147770 A1 | 5/2017 | Xu et al. | |
| 2018/0074054 A1 | 3/2018 | McPherson et al. | |
| 2018/0095091 A1 | 4/2018 | Wang | |
| 2018/0105880 A1 | 4/2018 | Genovese et al. | |
| 2018/0110455 A1 | 4/2018 | Chang et al. | |
| 2018/0235467 A1 | 8/2018 | Celenk et al. | |
| 2018/0253840 A1* | 9/2018 | Tran | G16H 40/63 |
| 2019/0313903 A1* | 10/2019 | McKinnon | G16H 50/20 |
| 2020/0005900 A1* | 1/2020 | Cha | G16H 10/40 |
| 2021/0038165 A1 | 2/2021 | Bergman et al. | |

FOREIGN PATENT DOCUMENTS

| | | |
|---|---|---|
| KR | 20160131453 | 11/2016 |
| RU | 2342074 | 12/2008 |
| RU | 2011146409 | 5/2013 |
| UA | 58034 | 3/2011 |
| WO | WO 2012/068545 | 5/2012 |
| WO | WO 2017/214203 | 12/2017 |
| WO | WO 2018/060996 | 4/2018 |
| WO | WO 2018/076284 | 5/2018 |
| WO | WO 2018/112198 | 6/2018 |

OTHER PUBLICATIONS

Devamalar et al., "An Architecture for a Fully Automated Real-Time Web-Centric Expert System," World Academy of Science, Engineering and Technology, 2007, 35:34-38.

Goh et al., "Retinal Imaging Techniques for Diabetic Retinopathy Screening," J Diabetes Sci Technol, Mar. 2016, 10(2): 282-294.

nybpinc.com [online], "Corporate Wellness," retrieved on Dec. 14, 2018, retrieved at URL <https://www.nybpinc.com/corporate-wellness-program>, 10 pages.

PCT International Search Report and Written Opinion in International Appln. No. PCT/US2020/043702, mailed Nov. 3, 2020, 13 pages.

The Australian Kidney Foundation, "Annual Report 2012," Kidney Health Australia, Dec. 2011, 65 pages.

wellbeingpeople.com [online], "The Wellbeing Directory, " 2017, retrieved at URL <https://www.wellbeingpeople.com/app/uploads/2018/02/Wellbeing-Directory-2017-Email.pdf>, 44 pages.

Yip et al., "Retinal Vascular Imaging Markers and Incident Chronic Kidney Disease: A Prospective Cohort Study," Scientific Reports, Aug. 2017, 7(9374):1-9.

* cited by examiner

SYSTEMS AND METHODS FOR DETECTION OF POTENTIAL HEALTH ISSUES

CROSS-REFERENCE TO RELATED APPLICATIONS

This application is a continuation application of and claims the benefit of priority under 35 U.S.C. § 121 to U.S. application Ser. No. 16/534,319, filed on Aug. 7, 2019, now U.S. Pat. No. 11,350,887, the contents of which are hereby incorporated by reference.

TECHNICAL FIELD

This disclosure generally relates to detection of potential health issues, such as chronic kidney disease.

BACKGROUND

Kidneys typically function to filter wastes and excess fluids from a person's blood, which are then excreted in a person's urine. When a person's kidneys lose their filtering capabilities, dangerous levels of fluid, electrolytes, and wastes can build up in the person's body. Chronic kidney disease (CKD) is a condition characterized by gradual loss of kidney function over time. CKD includes conditions that damage kidneys and decrease their ability to keep a person healthy. As CKD advances, wastes can build to high levels in blood and make the affected person feel sick. Affected persons may also develop complications like high blood pressure, anemia (low blood count), weak bones, poor nutritional health, and nerve damage. Also, kidney disease increases the risk of having heart and blood vessel disease. These problems may happen slowly over a long period of time. CKD may be caused by diabetes, high blood pressure, and other disorders. When kidney disease progresses, it may eventually lead to kidney failure, which requires dialysis or a kidney transplant to maintain life.

CKD is typically classified using five severity based stages. End stage renal disease (ESRD) is the last stage (stage five) of CKD. At this stage, kidneys are only functioning at 10 to 15 percent of their normal capacity. When CKD develops into ESRD, dialysis or a kidney transplant is necessary to stay alive. In many instances, detection and treatment can keep CKD from getting worse.

SUMMARY

In at least one aspect of the present disclosure a device for detecting potential health issues is provided. The device includes a retinal scanner configured to capture retinal data of the user. The device includes a blood pressure sensor configured to capture blood pressure data of the user. The device includes an alert module configured to alert the user of a potential health risk. The device includes a computer-readable medium comprising computer-executable instructions. The device includes at least one processor communicatively coupled to the retinal scanner, the blood pressure sensor, and the alert module, the at least one processor configured to execute the computer-executable instructions. When the at least one processor is executing the computer-executable instructions, the at least one processor is configured to carry out one or more operations. The one or more operations include receiving, from the retinal scanner, the retinal data of the user. The one or more operations include receiving, from the blood pressure sensor, the blood pressure data of the user. The one or more operations include detecting, based on the received retinal and blood pressure data, a potential health issue of the user. The one or more operations include causing, responsive to detecting the potential health issue of the user, the alert module to alert the user of the potential health issue.

The device can include a weight sensor communicatively coupled to the at least one processor and configured to capture weight data of the user. The one or more operations can include receiving, from the weight sensor, the weight data of the user. Detecting the potential health issue of the user can be based on the received weight data. The device can include a urinalysis sensor communicatively coupled to the at least one processor and configured to capture urinalysis data of the user. The one or more operations can include receiving, from the urinalysis sensor, the urinalysis data of the user. Detecting the potential health issue of the user can be based on the received urinalysis data. The device can include a user interface configured to capture lifestyle data of the user. The one or more operations can include receiving, from the user interface, the lifestyle data of the user. Detecting the potential health issue of the user is further based on the received lifestyle data.

Causing the alert module to alert the user of the potential health issue can include causing the alert module to recommend to the user that the user visit a healthcare provider. Causing the alert module to alert the user of the potential health issue can include generating a print-out having a summary of a plurality of risk factors.

The one or more operations can include determining, based on the received data, a health risk value. Detecting the potential health issue can include comparing the health risk value to a threshold health risk value. Determining the health risk value can include weighting the received data in accordance with a predetermined weighting scheme. Detecting the potential health issue of the user can include detecting that the user is at risk of having chronic kidney disease.

These and other aspects, features, and implementations can be expressed as methods, apparatus, systems, components, program products, methods of doing business, means or steps for performing a function, and in other ways, and will become apparent from the following descriptions, including the claims.

Implementations can include one or more of the following advantages. Kiosk technology can be used to address public health on a large-scale by facilitating early detection of potential health issues and, in some instances, encouraging people who may not otherwise be aware of their potential health issues to seek medical attention. A potential health issue can refer to a physical condition caused by diseases such as CKD or diabetes. The systems and methods can improve the accuracy of detection by using one or more types of sensors that provide data about a person that can be useful in determining if that person has potential health issues. For example, the systems and methods described in this specification can capture sensor data indicating whether or not a user exhibits certain risk factors that can indicate a potential health issue. A risk factor can refer to physical conditions that may indicate symptoms of underlying diseases. For example, the presence of albumin in urine can be a risk factor that indicates the user may have CKD.

These and other aspects, features, and implementations will become apparent from the following descriptions, including the claims.

DETAILED DESCRIPTION

Figure 1:
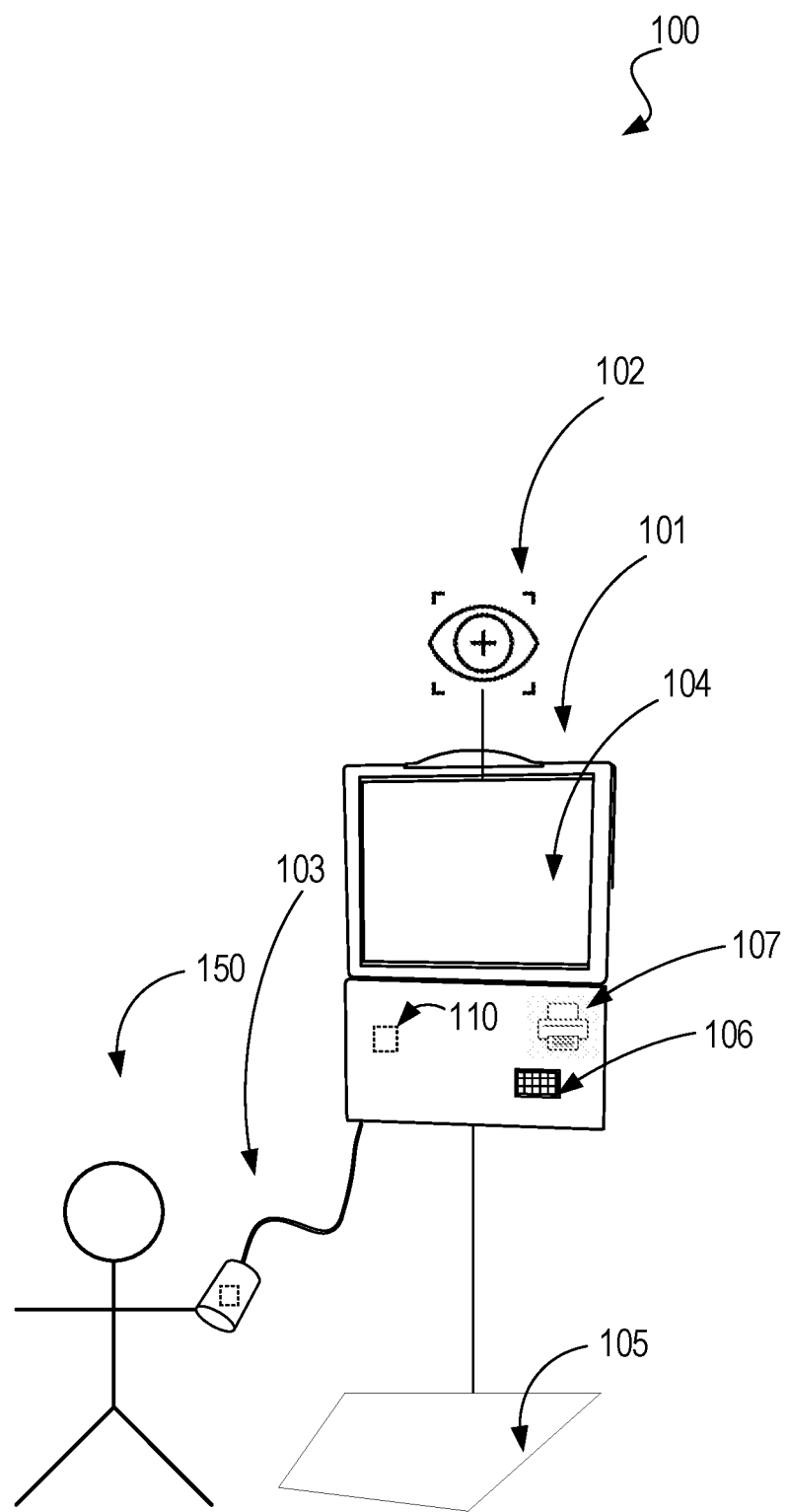
FIG. 1 shows an environment including a system for detecting potential health issues, in accordance with one or more embodiments of the present disclosure.

It is common to not experience symptoms of CKD in the early stages of CKD development. Because of this, CKD may not be detected until it has advanced to stage 5 (i.e., ESRD) in many instances. For example, some studies estimate that less than 40% of people that have stage 4 CKD are aware of their condition. Furthermore, the awareness rate decreases for people with earlier stage CKD (e.g., some studies estimate that the awareness rate for stage 2 CKD is less than 20%). As a result, CKD is typically not detected and treated until it advances to ESRD, which can typically require dialysis or kidney transplants. Therefore, systems and methods that can facilitate early diagnosis to the public on a large scale can be desired.

The present disclosure provides systems and methods for detecting potential health issues, such as CKD. The systems and methods can be implemented with public kiosk technology. For example, the systems and methods can be used utilized in a public setting such as, an airport or supermarket, to help address public health issues at a large scale. In general, the systems and methods described herein can act as an initial screening for potential health issues, and make recommendations to visit a healthcare provider (HCP) if it is determined that a user has a potential health issue.

In the following description, for the purposes of explanation, numerous specific details are set forth in order to provide a thorough understanding of the present disclosure. It will be apparent, however, that the present disclosure may be practiced without these specific details. In other instances, well-known structures and devices are shown in block diagram form in order to avoid unnecessarily obscuring the present disclosure.

In the drawings, specific arrangements or orderings of schematic elements, such as those representing devices, modules, instruction blocks, and data elements, are shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some embodiments.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships, or associations between elements. For example, where a connecting element represents a communication of signals, data, or instructions, it should be understood by those skilled in the art that such element represents one or multiple signal paths (e.g., a bus), as may be needed, to affect the communication.

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as to not unnecessarily obscure aspects of the embodiments.

Several features are described hereafter that can each be used independently of one another or with any combination of other features. However, any individual feature may not provide any of the advantages discussed above or may provide one of the advantages discussed above. Although headings are provided, data related to a particular heading, but not found in the section having that heading, may also be found elsewhere in this description.

FIG. 1 shows an environment 100 including a system 101 for generating an anonymized acoustic fingerprint for the environment 100. As shown, the environment 100 is an airport terminal. However, the environment 100 can be any public or private setting, such as a supermarket, hospital waiting area, school auditorium, and so forth. The environment 100 includes a user 150 receiving treatment from a system 101 for detecting potential health issues. For illustrative purposes, the system 101 is described as detecting whether the user 150 is at risk of having or developing CKD. However, in some implementations, the system 101 can detect whether the user 150 is at risk of having or developing other health issues, such as diabetes, chronic heart disease, and so forth.

The system 101 includes a retinal scanner 102, a blood pressure sensor 103, a user interface 104, a weight sensor 105, a urinalysis sensor 106, an alert module 107, and one or more computer processors 110. The one or more computer processors 110 are communicatively coupled with the retinal scanner 102, blood pressure sensor 103, user interface 104, weight sensor 105, urinalysis sensor 106, and alert module 107. As discussed in more detail later with reference to FIG. 2, at least one of the retinal scanner 102, blood pressure sensor 103, user interface 104, weight sensor 105, or urinalysis sensor 106 can capture health data of the user 150, and transmit the health data to the one or more computer processors 110. Furthermore, as discussed in more detail later with reference to FIG. 2, the computer processors 110 can use the health data to determine if the user 150 is at risk of having CKD and cause the alert module 107 to alert the user 150 that the user 150 may be at risk of having or developing CKD. In some implementations, the system 101 can recommend that the user 150 visit a HCP. In some implementations, the system 101 can inquire as to whether the user 150 has a primary HCP, and, if the user 150 does not have a primary HCP, the system 101 can recommend to the user a primary HCP with the necessary qualifications for treating the detected potential health issues (i.e., CKD).

Figure 2:
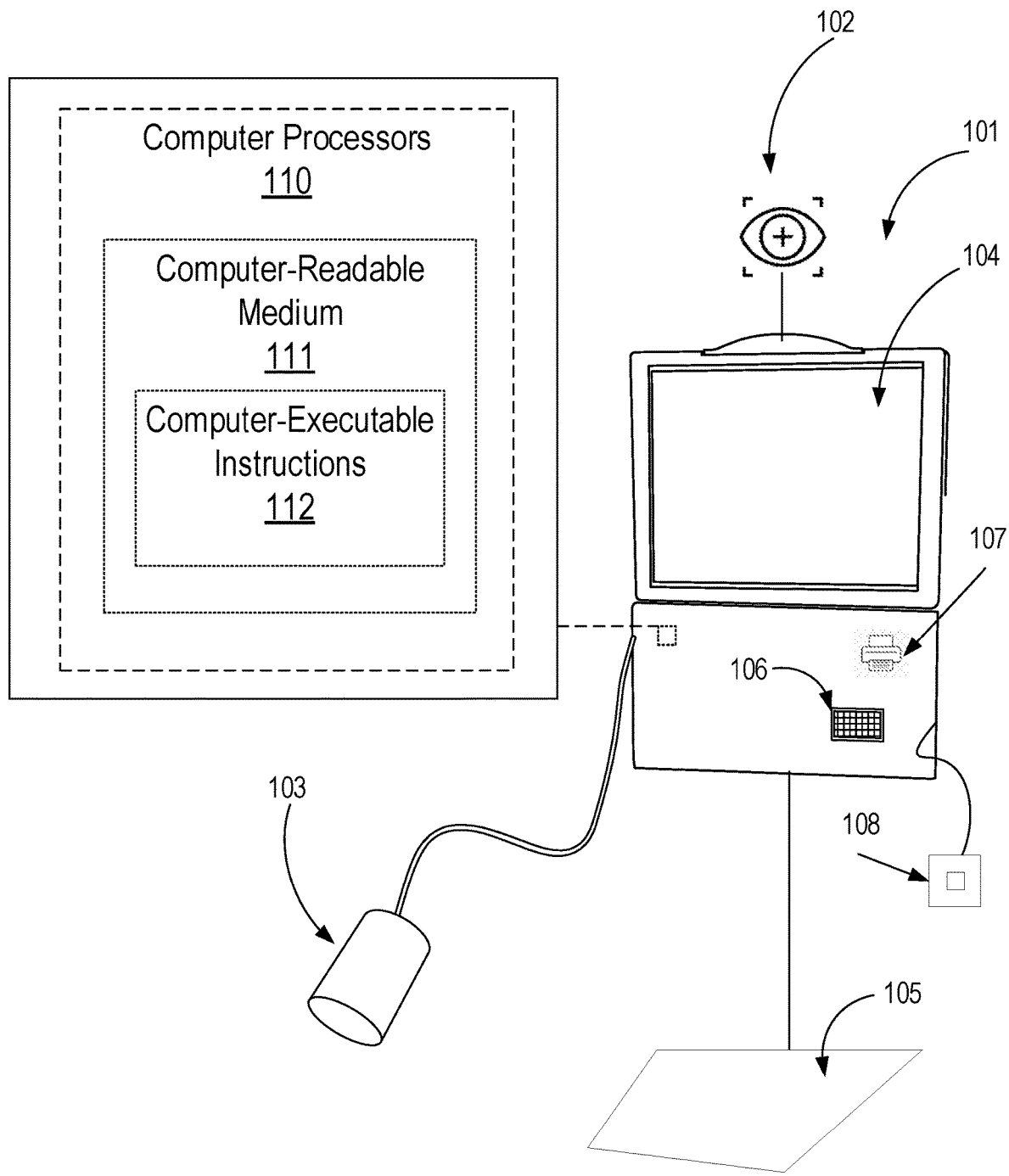
FIG. 2 shows a system for detecting potential health issues, in accordance with one or more embodiments of the present disclosure.

FIG. 2 shows the system 101 for detecting potential health issues, in accordance with one or more embodiments of the present disclosure. As indicated earlier, the system 101 includes a retinal scanner 102, a blood pressure sensor 103, a user interface 104, a weight sensor 105, a urinalysis sensor 106, an alert module 107, and one or more computer processors 110. In some implementations, the system 101 includes a bio-impedance sensor 108.

The retinal scanner 102 is configured to capture retinal data of a user. For example, the retinal scanner 102 can cast a beam of low-energy infrared light into the eye of the user as the user's eye is positioned in front of and in close proximity to the retinal scanner 102. The beam of infrared light can trace a standardized path on the retina of the user to capture a retinal image. In some implementations, the retinal scanner 102 compile unique features of the network of retinal blood vessels into a retinal template. For example, because retinal blood vessels are more absorbent of infrared light than the rest of the eye, which causes the amount of reflection to vary during the retinal scan, the retinal scanner 102 can encode this pattern of variations as a retinal template. In some implementations, the retinal scanner 102 is configured to perform optical coherence tomography (OCT), which can involve using light waves to capture high-resolution cross-section images of the retina. In some implementations, the retinal scanner 102 includes a a fundus camera, which refers to retinal imager that includes a specialized low power microscope with an attached camera designed to photograph the interior surface of the eye, including the retina, retinal vasculature, optic disc, macula, and posterior pole (i.e. the fundus).

The blood pressure sensor 103 is configured to capture blood pressure data of a user. In some implementations, the blood pressure sensor 103 is an electronic sphygmomanometer. A sphygmomanometer refers to a device that includes an inflatable cuff, in which a user typically places their arm, to collapse and then release the artery under the cuff in a controlled manner to measure systolic and diastolic blood pressure by oscillometric detection. Although shown as a sphygomanometer, in some implementations, the blood pressure sensor 103 is an optical sensor against which a user can press their finger (or forehead). For example, the blood pressure sensor 103 can utilize Photoplethysmography (PPG) to measure oxygen saturation, blood pressure, cardiac output and so forth. In some implementations, the optical sensor measures how light penetrating through the finger changes its characteristics and determine, based on these changing characteristics, a measurement of the user's blood pressure. In some implementations, the blood pressure sensor 103 is configured to measure oxygen saturation in the blood by using a pulse oximetry device that measures light absorption of hemoglobin. In some implementations, the blood pressure sensor 103 measures, using PPG, cardiac output, which refers to the product of the heart rate (or number of heart beats per minute) and the stroke volume (volume of blood pumped from the ventricle per beat). In some implementations, the blood pressure sensor 103 measures, using PPG, vascular resistance, which refers to the resistance that must be overcome to push blood through the circulatory system and create flow.

The user interface 104 includes a display device, such as an electronic display device. The display device can be configured to act as a touchscreen display device. In some implementations, the user interface 104 is a graphical user interface (GUI). The user interface 104 is configured to allow a user of the system 101 to interact with the system 101 through graphical icons and visual indicators. For example, the user interface 104 can use windows, icons, menus, pointer paradigm (WIMP) to allow a user to interact with the system 101. In some implementations, the user interface 104 cooperates with the display device to provide a user with a touchscreen GUI. Additionally, or alternatively, the user interface can include one or more input devices such as a mouse and/or keyboard communicatively coupled with the system 101. The user interface 104 can also use a post-WIMP paradigm typically found in touchscreen-based GUIs. In some implementations, the user interface 104 is configured to display images in the form of still photographs and/or videos.

The user interface 104 is configured to capture lifestyle data of a user of the system 101. Lifestyle data can represent voluntary choices of a user, such as alcohol usage and tobacco usage. Additionally, or alternatively, lifestyle data can represent biological or inherited features of a user, such as race, ethnicity, height, and family medical history. For example, the user interface 104 can present a set of questions to a user. The questions can be helpful in determining if the user has is at risk of having or developing a health issue, such as CKD. For example, the user interface 104 can prompt a user to answer questions related to the user's age, height, race, ethnicity, tobacco usage, family history of kidney disease, alcohol usage, diabetic history, and so forth. The user interface 104 can also prompt a user to answer questions related to whether the user has been experiencing nausea, vomiting, loss of appetite, fatigue, sleep problems, changes in urination frequency, decreased mental sharpness, muscle cramps, persistent itching, chest pain, swelling of feed or ankles, shortness of breath, and so forth. A user can answer the questions using, for example, the touchscreen functionality of the user interface 104 and/or a keyboard and mouse of the user interface 104. In some implementations, the questions are provided in a scrolling window on the user interface 104, which can increase computational efficiency of the system 101, as a scrolling window is capable of reducing the need to load multiple individual pages.

An example list of questions that can be presented to a user through the user interface 104 include, but are not limited to, the following:

1. How old are you?
2. Has a doctor ever told you that you have diabetes or pre-diabetes?
    i. If yes, what was your A1C test result?
       [I don't know]; [Below 5]; [Between 5-6]; [Between 6-7]; [Above 7];
3. Approximately how often do you need to wake up in the night to urinate?
    [Rarely or Never]; [Sometimes]; [A few times a week]; [Once every night]; [Many times every night];
4. Has a doctor ever told you that you have high blood pressure?
    [No]; [Yes, 10 or more years ago]; [Yes, 5 or more years ago]; [Yes, in the last few years, but less than 5];
5. Do you know of any blood relative(s) who have had kidney disease (select all that apply)?
    [Mother] [Father] [Brother/Sister] [Aunt/Uncle] [Cousin] [None]
6. Please select each button that indicates how much each of the sentences below applies to you:
    i. I find that I need to urinate more often, especially at night:
    [Rarely]; [Often]; [Almost Always]
    ii. I have more swelling of my feet and ankles than I remember in the past: [Rarely]; [Often]; [Almost Always]
    iii. I have dry/itchy skin: [Rarely]; [Often]; [Almost Always]

iv. I have muscle cramps at night: [Rarely]; [Often]; [Almost Always]
v. I have trouble concentrating: [Rarely]; [Often]; [Almost Always]
vi. I have trouble sleeping: [Rarely]; [Often]; [Almost Always]
vii. I feel tired: [Rarely]; [Often]; [Almost Always]
viii. I feel cold even when others are not: [Rarely]; [Often]; [Almost Always]
ix. My urine is foamy or bubbly: [Rarely]; [Often]; [Almost Always].

The weight sensor 105 is configured to capture weight data of a user. For example, the weight sensor 105 can be a digital weighing scale on which a user can stand or sit. When the user stands or sits on the weighing scale, the weighing scale can measure the weight of the user. For example, the force produced by the user's weight can cause a spring of the weighing scale to deform, and the amount of deformation can be measured by one or more transducers called strain gauges. A strain gauge is a conductor whose electrical resistance changes when its length changes.

The urinalysis sensor 106 is configured to capture urinalysis data of the user. For example, the urinalysis sensor 106 can include a slot configured to receive a vial of urine and a urine dipstick. A urine dipstick is a specially treated chemical strip having patches that, in response to being placed in the vial, changes colors to indicate the presence of abnormalities in the urine, such as excessive amounts of protein, blood, pus, bacteria, sugar, and white blood cells. In some implementations, the urinalysis sensor 106 includes actuators and other mechanisms that, once the urine vial is received, dips a pre-loaded dipstick into the urine vial. The urinalysis sensor 106 can also include optical equipment configured to detect the color changes on the patches of the dipstick.

The alert module 107 is configured to alert a user of a potential health issue. For example, the alert module 107 includes a printer, such as a toner-based printer, liquid inkjet printer, solid ink printer, and so forth. The alert module 107 provides a user with a read-out (i.e., a paper having representations of graphics and/or text) representing output from the computer processors 110, as will be described later in more detail. Additionally, or alternatively, the alert module 107 is integrated with the user interface 104. For example, the user interface 104 can display graphical representations and text representing output from the computer processors 110. Additionally, or alternatively, the alert module 107 can provide audible output for alerting the user of a potential health issue.

The bio-impedance sensor 108 is configured to capture and transmit hydration data of a user by determining a user's hydration status by measuring the impedance of a weak current flowing through the user's body due to body's water and electrolyte content. For example, the bio-impedance sensor 108 can include an electrode for sending a weak current through a user's body and can measure the amount of total body water in the user based on the measured impedance.

The computer processors 110 include a computer-readable medium 111. The computer-readable medium 111 includes computer-executable instructions 112. The computer-readable medium 111 (or computer-readable memory) can include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM), and the like. In some implementations, the computer-readable medium 111 includes code-segment having executable instructions.

The computer processors 110 are communicatively coupled to the one or more acoustic sensors 120. In some implementations, the computer processors 110 include a general purpose processor. In some implementations, the computer processors 110 include a central processing unit (CPU). In some implementations, the computer processors 110 include at least one application specific integrated circuit (ASIC). The computer processors 110 can also include general purpose programmable microprocessors, special-purpose programmable microprocessors, digital signal processors (DSPs), programmable logic arrays (PLAs), field programmable gate arrays (FPGA), special purpose electronic circuits, etc., or a combination thereof. The computer processors 110 are configured to execute program code means such as the computer-executable instructions 112.

When the computer processors 110 execute the computer-executable instructions 112, the computer processors 110 carry out one or more operations. When the computer processors 110 execute the computer-executable instructions 112, the computer processors 110 are configured to receive health data of a user.

When the computer processors 110 execute the computer-executable instructions 112, the computer processors 110 are configured to receive, from the retina scanner 102, retinal data of a user. For example, as previously indicated, the retinal scanner 102 can capture high-resolution images of a user's retina. The computer processors 110 are configured to receive retinal data representing these images and extract certain biomarkers presented by the images that may indicate the presence of certain diseases such as CKD, diabetes, and so forth. For example, in some implementations, the computer processors 110 are capable of measuring, based on the received retinal image data, the volume of the retina, total thickness of the retina, and/or central subfield mean retinal thickness. These measurements can specify the presence of retinopathy (i.e., retinal disease) by indicating the presence of characteristic lesions of the retina, such as microaneurysms, hemorrhages, cotton wool spots, intraretinal microvascular abnormalities, hard exudates, venous beading, and so forth. The presence of these characteristic lesions may indicate that the user is at risk of having, for example, diabetes and/or chronic kidney disease.

When the computer processors 110 execute the computer-executable instructions 112, the computer processors 110 are configured to receive, from the blood pressure sensor 103, blood pressure data of a user. As indicated previously, the blood pressure sensor 103 can measure the systolic and/or diastolic blood pressure of a user. The blood pressure sensor 103 is capable of transmitting blood pressure data representing values in accordance with these measurements to the computer processors 110. High blood pressure may indicate that user is at risk of having or developing certain diseases, such as chronic kidney disease and diabetes. In some instances, high blood pressure is defined as systolic blood pressure measurement over 130 and a diastolic blood pressure measurement over 80. As indicated earlier, the blood pressure data can also (or alternatively) include pulse measurements, cardiac output measurements, vascular resistance measurements, oxygen saturation measurements, and so forth.

When the computer processors 110 execute the computer-executable instructions 112, the computer processors 110 are configured to receive, from the user interface 104, lifestyle data of the user. For example, as indicated previously, the user interface 104 can receive, from a user, answers to questions related to the user's age, height, race, ethnicity, tobacco usage, family history of kidney disease/diabetes, alcohol usage, diabetic history, and whether the user has been experiencing nausea, vomiting, loss of appetite, fatigue, sleep problems, changes in urination frequency, decreased mental sharpness, muscle cramps, persistent itching, chest pain, swelling of feed or ankles, shortness of breath, and so forth. The user interface 104 is capable of transmitting lifestyle data indicating answers to these questions to the computer processors 110. The answers to these questions may indicate a risk of the user having certain diseases. For example, older age, frequent tobacco use, and incidences of nausea may indicate that a user is at risk of having or developing chronic kidney disease or diabetes.

When the computer processors 110 execute the computer-executable instructions 112, the computer processors 110 are configured to receive, from the weight sensor 105, weight data of a user. For example, as indicated previously, the weight sensor 105 can measure the weight of a user. The weight sensor 105 is capable of transmitting weight data indicating the measured weight of a user to the computer processors 110. A user's weight may indicate that the user is at risk of having or developing chronic kidney disease and/or diabetes. For example, the computer processors 110 can determine a body mass index (BMI) of a user by using the user's measured weight and height measurements (e.g., as indicated by the user's answers received from the user interface 104 to questions related to the user's height). A high BMI (e.g., BMI value of 25 or greater) may indicate that a user is at risk of developing CKD or diabetes.

When the computer processors 110 execute the computer-executable instructions 112, the computer processors 110 are configured to receive, from the urinalysis sensor 106, urinalysis data of a user. For example, as indicated previously, the urinalysis sensor 106 can detect color changes on a dipstick used in a urine dipstick test that can indicate the presence of abnormalities in the urine (e.g., excessive amounts of protein, blood, pus, bacteria, sugar, white blood cells, etc.). The urinalysis sensor 106 is capable of transmitting urinalysis data representing the color changes corresponding to the dipstick to the computer processors 110. The presence of abnormalities in the urine may indicate that a user is at risk of having or developing CKD or diabetes. For example, the presence of certain proteins in urine, such as albumin, may indicate early signs of CKD. As another example, the presence of excess sugar (e.g., greater than 0.8 millimoles/liter) may indicate that a user is at risk of having or developing CKD or diabetes.

When the computer processors 110 execute the computer-executable instructions 112, the computer processors 110 are configured to receive, from the bio-impedance sensor 108, hydration data of the user. As indicated above, the hydration data can reflect a measurement of the amount of total body water in the user based on the measured impedance.

When the computer processors 110 execute the computer-executable instructions 112, the computer processors 110 are configured to detect, based on the received health data of a user, a potential health issue of the user (e.g., whether the user is at risk of having or developing CKD and/or diabetes). For example, if the received data indicates a high BMI, presence of albumin in the urine, frequent tobacco usage, and a family history of kidney disease, the computer processors 110 can determine that the corresponding user is at risk of having or developing CKD. In some implementations, the received data is assigned values. For example, a value can be assigned to the measured BMI (e.g., a "1" for a BMI of 18 or lower, a "2" for a BMI of 18-24, a "3" for a BMI of 25-29, and a "4" for a BMI of over 30). As another example, a value can be assigned to the answers to each question (e.g., a "1" for a yes answer and a "0 for a no answer). In some implementations, the computer processors 110 combine (e.g., sum, average, determine median, etc.) the assigned values to generate a health risk value and compare the health risk value to a threshold health risk value. If the health risk value exceeds the threshold health risk value, the computer processors 110 determine that the user is at risk of having or developing a potential health issue (e.g., CKD, diabetes, etc.). In some implementations, the computer processors 110 weight the assigned values. The weighting of the assigned values can be based on, for example, the predictive power of the underlying data for predicting whether or not a user is at risk of having or developing a potential health issue. For example, the presence of albumin in urine may be more predictive as to whether a user is at risk of having or developing CKD than a high BMI. Therefore, the values corresponding to the presence of albumin in urine can be weighted heavier than the values corresponding to a high BMI. In some implementations, the weighting scheme weights certain measurements in accordance with the following ranking (from highest to lowest):

1. Blood Pressure/Pulse measurement;
2. Hydration Status;
3. Retinal scan analysis;
4. Cardiac rhythm;
5. Cardiac output;
6. Peripheral vascular resistance;
7. Oxygen saturation.

When the computer processors 110 execute the computer-executable instructions 112, the computer processors 110 are configured to cause the alert module 107 to alert a user of a potential health issue in response to detecting the potential health issue of the user. For example, if the computer processors 110 detect that a user is at risk of having or developing CKD, the computer processors 110 can cause the alert module 107 to generate a print-out stating: "Based on the received input, it has been determined that you are at risk of having or developing chronic kidney disease. Please present this print-out to a health care provider for further information." In some implementations, the print-out also lists the risk factors that lead to the determination (e.g., high BMI, albumin in urine, frequent smoking, etc.). As indicated earlier, this alert can be alternatively (or additionally) be provided by the user interface 104. In some implementations, the computer processors 110 can utilize a database (e.g., local, cloud-based, etc.) to help the user locate a healthcare professional that specialize in the detected potential health issue. For example, if the detected potential health issue is that the user is a risk of having CKD, the computer processors can utilize the database to identify one or more nephrologist that are local to the user's place of residency (e.g., within 60 miles of the user's place of residency). For determining the user's place of residency, the user interface 104 can prompt the user to provide, for example, their home address.

While the system 101 has been described as having a retinal scanner 102, a blood pressure sensor 103, a user interface 104, a weight sensor 105, a urinalysis sensor 106, and a bio-impedance sensor 108, the system 101 can have more or less of these components. For example, in some implementations, the system 101 can include two retinal scanners 102. In some implementations, the system 101 does not include a user interface 104, the urinalysis sensor 106, and/or the weight sensor 104. In some implementations, the system 101 does not include the retinal scanner 102. Consequently, the computer processors 110 can be configured to detect potential health issues based on the data available in accordance with the configuration of sensors/scanners of the system 101.

Figure 3:
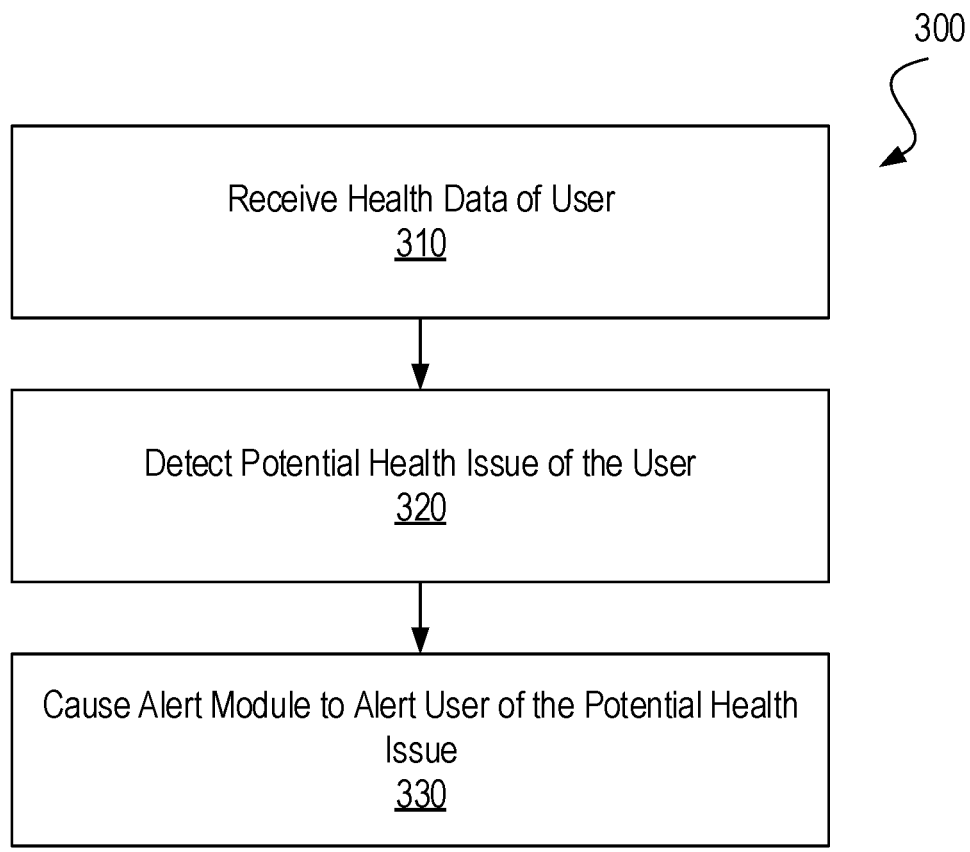
FIG. 3 shows a flowchart depicting an example of a method for detecting potential health issues, in accordance with one or more embodiments of the present disclosure.

FIG. 3 shows a flowchart depicting an example of a method 300 for detecting potential health issues, in accordance with one or more embodiments of the present disclosure. For illustrative purposes, the method 300 is described as being performed by the system 101 for detecting potential health issues described previously with reference to FIG. 2. The method 300 includes receiving health data of a user (block 310), detecting a potential health issue of the user (block 320), and causing an alert module to alert the user of the potential health issue (block 330).

At block 310, the computer processors 110 receive health data of a user. For example, as previously indicated with reference to FIG. 2, the computer processors 110 can receive: retinal data from the retina scanner 102, blood pressure data from the blood pressure sensor 103, lifestyle data from the user interface 104, weight data from the weight sensor 105, and/or urinalysis data from the urinalysis sensor 106.

At block 320, the computer processors 110 detect, based on the received health data of the user, a potential health issue of the user (e.g., whether the user is at risk of having or developing CKD and/or diabetes). For example, if the received data indicates a high BMI, presence of albumin in the urine, frequent tobacco usage, and a family history of kidney disease, the computer processors 110 can determine that the corresponding user is at risk of having or developing CKD. In some implementations, the received data is assigned values. For example, a value can be assigned to the measured BMI (e.g., a "1" for a BMI of 18 or lower, a "2" for a BMI of 18-24, a "3" for a BMI of 25-29, and a "4" for a BMI of over 30). As another example, a value can be assigned to the answers to each question (e.g., a "1" for a yes answer and a "0 for a no answer). In some implementations, the computer processors 110 combine (e.g., sum, average, determine median, etc.) the assigned values to generate a health risk value and compare the health risk value to a threshold health risk value. If the health risk value exceeds the threshold health risk value, the computer processors 110 determine that the user is at risk of having or developing a potential health issue (e.g., CKD, diabetes, etc.). In some implementations, the computer processors 110 weight the assigned values. The weighting of the assigned values can be based on, for example, the predictive power of the underlying data for predicting whether or not a user is at risk of having or developing a potential health issue. For example, the presence of albumin in urine may be more predictive as to whether a user is at risk of having or developing CKD than a high BMI. Therefore, the values corresponding to the presence of albumin in urine can be weighted heavier than the values corresponding to a high BMI.

At block 330, the computer processors 110 cause the alert module 107 to alert the user of a potential health issue in response to detecting the potential health issue of the user. For example, if the computer processors 110 detect that the user is at risk of having or developing CKD, the computer processors 110 can cause the alert module 107 to generate a print-out stating: "Based on the received input, it has been determined that you are at risk of having or developing chronic kidney disease. Please present this print-out to a health care provider for further information." In some implementations, the print-out also lists the risk factors that lead to the determination (e.g., high BMI, albumin in urine, frequent smoking, etc.). As indicated earlier, this alert can be alternatively (or additionally) be provided by the user interface 104. In some implementations, the computer processors 110 can utilize a database (e.g., local, cloud-based, etc.) to help the user locate a healthcare professional that specialize in the detected potential health issue. For example, if the detected potential health issue is that the user is a risk of having CKD, the computer processors can utilize the database to identify one or more nephrologist that are local to the user's place of residency (e.g., within 60 miles of the user's place of residency). For determining the user's place of residency, the user interface 104 can prompt the user to provide, for example, their home address.

Figure 4:
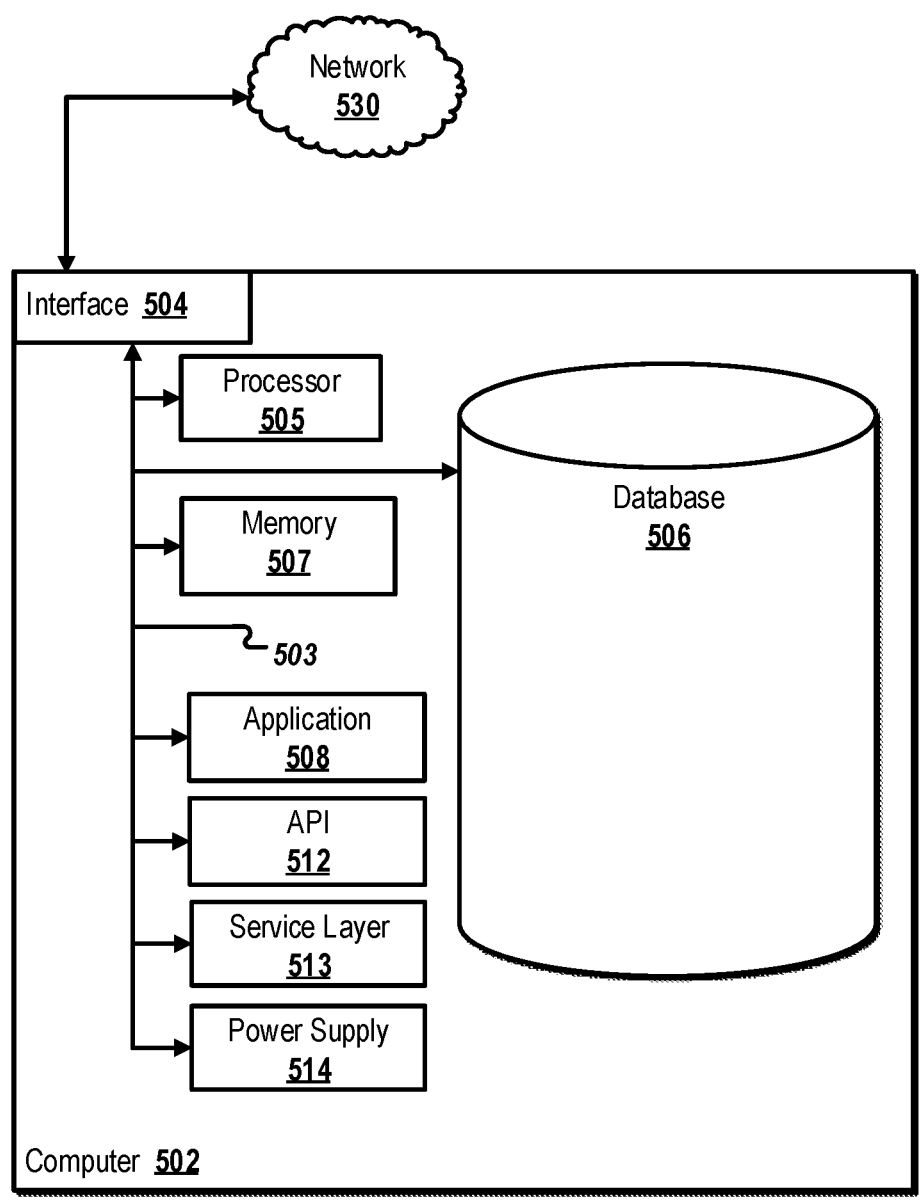
FIG. 4 is a block diagram of an example computer system used to provide computational functionalities associated with described algorithms, methods, functions, processes, flows, and procedures described in the present disclosure.

FIG. 4 is a block diagram of an example computer system 500 used to provide computational functionalities associated with described algorithms, methods, functions, processes, flows, and procedures described in the present disclosure (such as the method 300 described previously with reference to FIG. 3), according to some implementations of the present disclosure. The illustrated computer 502 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 502 can include input devices such as keypads, keyboards, and touch screens that can accept user information. Also, the computer 502 can include output devices that can convey information associated with the operation of the computer 502. The information can include digital data, visual data, audio information, or a combination of information. The information can be presented in a graphical user interface (UI) (or GUI).

The computer 502 can serve in a role as a client, a network component, a server, a database, a persistency, or components of a computer system for performing the subject matter described in the present disclosure. The illustrated computer 502 is communicably coupled with a network 530. In some implementations, one or more components of the computer 502 can be configured to operate within different environments, including cloud-computing-based environments, local environments, global environments, and combinations of environments.

At a high level, the computer 502 is an electronic computing device operable to receive, transmit, process, store, and manage data and information associated with the described subject matter. According to some implementations, the computer 502 can also include, or be communicably coupled with, an application server, an email server, a web server, a caching server, a streaming data server, or a combination of servers.

The computer 502 can receive requests over network 530 from a client application (for example, executing on another computer 502). The computer 502 can respond to the received requests by processing the received requests using software applications. Requests can also be sent to the computer 502 from internal users (for example, from a command console), external (or third) parties, automated applications, entities, individuals, systems, and computers.

Each of the components of the computer 502 can communicate using a system bus 503. In some implementations, any or all of the components of the computer 502, including hardware or software components, can interface with each other or the interface 504 (or a combination of both), over the system bus 503. Interfaces can use an application programming interface (API) 512, a service layer 513, or a combination of the API 512 and service layer 513. The API 512 can include specifications for routines, data structures, and object classes. The API 512 can be either computer-language independent or dependent. The API 512 can refer to a complete interface, a single function, or a set of APIs.

The service layer 513 can provide software services to the computer 502 and other components (whether illustrated or not) that are communicably coupled to the computer 502. The functionality of the computer 502 can be accessible for all service consumers using this service layer. Software services, such as those provided by the service layer 513, can provide reusable, defined functionalities through a defined interface. For example, the interface can be software written in JAVA, C++, or a language providing data in extensible markup language (XML) format. While illustrated as an integrated component of the computer 502, in alternative implementations, the API 512 or the service layer 513 can be stand-alone components in relation to other components of the computer 502 and other components communicably coupled to the computer 502. Moreover, any or all parts of the API 512 or the service layer 513 can be implemented as child or sub-modules of another software module, enterprise application, or hardware module without departing from the scope of the present disclosure.

The computer 502 includes an interface 504. Although illustrated as a single interface 504 in FIG. 4, two or more interfaces 504 can be used according to particular needs, desires, or particular implementations of the computer 502 and the described functionality. The interface 504 can be used by the computer 502 for communicating with other systems that are connected to the network 530 (whether illustrated or not) in a distributed environment. Generally, the interface 504 can include, or be implemented using, logic encoded in software or hardware (or a combination of software and hardware) operable to communicate with the network 530. More specifically, the interface 504 can include software supporting one or more communication protocols associated with communications. As such, the network 530 or the interface's hardware can be operable to communicate physical signals within and outside of the illustrated computer 502.

The computer 502 includes a processor 505. Although illustrated as a single processor 505 in FIG. 4, two or more processors 505 can be used according to particular needs, desires, or particular implementations of the computer 502 and the described functionality. Generally, the processor 505 can execute instructions and can manipulate data to perform the operations of the computer 502, including operations using algorithms, methods, functions, processes, flows, and procedures as described in the present disclosure.

The computer 502 also includes a database 506 that can hold data for the computer 502 and other components connected to the network 530 (whether illustrated or not). For example, database 506 can be an in-memory, conventional, or a database storing data consistent with the present disclosure. In some implementations, database 506 can be a combination of two or more different database types (for example, hybrid in-memory and conventional databases) according to particular needs, desires, or particular implementations of the computer 502 and the described functionality. Although illustrated as a single database 506 in FIG. 4, two or more databases (of the same, different, or combination of types) can be used according to particular needs, desires, or particular implementations of the computer 502 and the described functionality. While database 506 is illustrated as an internal component of the computer 502, in alternative implementations, database 506 can be external to the computer 502.

The computer 502 also includes a memory 507 that can hold data for the computer 502 or a combination of components connected to the network 530 (whether illustrated or not). Memory 507 can store any data consistent with the present disclosure. In some implementations, memory 507 can be a combination of two or more different types of memory (for example, a combination of semiconductor and magnetic storage) according to particular needs, desires, or particular implementations of the computer 502 and the described functionality. Although illustrated as a single memory 507 in FIG. 4, two or more memories 507 (of the same, different, or combination of types) can be used according to particular needs, desires, or particular implementations of the computer 502 and the described functionality. While memory 507 is illustrated as an internal component of the computer 502, in alternative implementations, memory 507 can be external to the computer 502.

The application 508 can be an algorithmic software engine providing functionality according to particular needs, desires, or particular implementations of the computer 502 and the described functionality. For example, application 508 can serve as one or more components, modules, or applications. Further, although illustrated as a single application 508, the application 508 can be implemented as multiple applications 508 on the computer 502. In addition, although illustrated as internal to the computer 502, in alternative implementations, the application 508 can be external to the computer 502.

The computer 502 can also include a power supply 514. The power supply 514 can include a rechargeable or non-rechargeable battery that can be configured to be either user- or non-user-replaceable. In some implementations, the power supply 514 can include power-conversion and management circuits, including recharging, standby, and power management functionalities. In some implementations, the power-supply 514 can include a power plug to allow the computer 502 to be plugged into a wall socket or a power source to, for example, power the computer 502 or recharge a rechargeable battery.

There can be any number of computers 502 associated with, or external to, a computer system containing computer 502, with each computer 502 communicating over network 530. Further, the terms "client," "user," and other appropriate terminology can be used interchangeably, as appropriate, without departing from the scope of the present disclosure. Moreover, the present disclosure contemplates that many users can use one computer 502 and one user can use multiple computers 502.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/-R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component (for example, as a data server), or that includes a middleware component (for example, an application server). Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of these systems and methods have been described. Nevertheless, it will be understood that various modifications may be made without departing from the spirit and scope of this disclosure.

What is claimed is:

1. A device for detecting potential kidney diseases, comprising:
   at least one sensor configured to capture sensor data corresponding to a user;
   an audible or visual indicator; and
   at least one processor communicatively coupled to the at least one sensor and the audible or visual indicator, the at least one processor configured to execute non-transitory computer-executable instructions that, when executed, cause the at least one processor to carry out operations comprising:
      causing the at least one sensor to capture sensor data corresponding to the user, the captured sensor data comprising retinal image data of the user;
      receiving, at the at least one processor from the at least one sensor, the captured sensor data;
      processing, by the at least one processor, the captured sensor data to determine at least one of a cardiac output of the user or a hydration status of the user;
      processing, by the at least one processor, the retinal image data to measure at least one of a volume of a retina of the user, a total thickness of the retina of the user, or a central subfield mean retinal thickness;

determining, by the at least one processor based on the processed retinal image data and the at least one of the cardiac output of the user or the hydration status of the user, a risk that the user has at least one kidney disease; and transmitting, by the at least one processor, a signal representing the risk that the user has at least one kidney disease to the audible or visual indicator for presenting the risk to the user.

2. The device of claim 1, wherein:

the at least one sensor comprises a weight sensor communicatively coupled to the at least one processor; and determining a risk that the user has at least one kidney disease is further based on processing, by the at least one processor, the captured sensor data to determine the weight of the user.

3. The device of claim 1, wherein:

the at least one sensor comprises a urinalysis sensor communicatively coupled to the at least one processor; and determining a risk that the user has at least one kidney disease is further based on processing, by the at least one processor, the captured sensor data to determine urinalysis data of the user.

4. The device of claim 1, wherein presenting the risk to the user comprises presenting, by the audible or visual indicator to the user, a recommendation that the user visit a healthcare provider.

5. The device of claim 1, wherein determining the risk that the user has at least one kidney disease further comprises:

processing the captured sensor data to determine a health risk value; and comparing the health risk value to a threshold health risk value.

6. The device of claim 5, wherein determining the health risk value comprises weighting the processed sensor data in accordance with a predetermined weighting scheme.

7. The device of claim 1, wherein presenting the risk to the user comprises generating a print-out having a summary of a plurality of risk factors.

8. The device of claim 1, further comprising a user interface configured to capture lifestyle data of the user, wherein the operations further comprise:

receiving, from the user interface, lifestyle data of the user; and the risk that the user has at least one kidney disease is determined based partly on the received lifestyle data.

9. The device of claim 1, wherein determining the risk that the user has at least one kidney disease comprises determining a risk that the user has chronic kidney disease.

10. The device of claim 1, wherein:

processing the retinal image data comprises processing, by the at least one processor, the retinal image data to measure the volume of the retina of the user; and determining the risk that the user has at least one kidney disease comprises determining, by the at least one processor based on the volume of the retina of the user and the at least one of the cardiac output of the user or the hydration status of the user, the risk that the user has at least one kidney disease.

11. A method, comprising:

causing at least one sensor to capture sensor data corresponding to a user, the captured sensor data comprising retinal image data of the user;

receiving, from the at least one sensor, the captured sensor data;

processing the captured sensor data to determine at least one of a cardiac output of the user or a hydration status of the user;

processing the retinal image data to measure at least one of a volume of a retina of the user, a total thickness of the retina of the user, or a central subfield mean retinal thickness;

determining, based on the processed retinal image data and the at least one of the cardiac output of the user or the hydration status of the user, a risk that the user has at least one kidney disease; and transmitting a signal representing the risk that the user has at least one kidney disease to an audible or visual indicator for presenting the risk to the user.

12. The method of claim 11, wherein:

the at least one sensor comprises a weight sensor; and determining a risk that the user has at least one kidney disease is further based on processing the captured sensor data to determine the weight of the user.

13. The method of claim 11, wherein:

the at least one sensor comprises a urinalysis sensor; and determining a risk that the user has at least one kidney disease is further based on processing the captured sensor data to determine urinalysis data of the user.

14. The method of claim 11, wherein presenting the risk to the user comprises causing the audible or visual indicator to present, to the user, a recommendation that the user visit a healthcare provider.

15. The method of claim 11, wherein determining the risk that the user has at least one kidney disease further comprises:

processing the captured sensor data to determine a health risk value; and comparing the health risk value to a threshold health risk value.

16. The method of claim 15, wherein determining the health risk value comprises weighting the processed sensor data in accordance with a predetermined weighting scheme.

17. The method of claim 11, further comprising, receiving, from a user interface, lifestyle data of the user, wherein the risk that the user has at least one kidney disease is determined based partly on the received lifestyle data.

18. The method of claim 11, wherein:

processing the retinal image data comprises processing the retinal image data to measure the volume of the retina of the user; and determining the risk that the user has at least one kidney disease comprises determining, based on the volume of the retina of the user and the at least one of the cardiac output of the user or the hydration status of the user, the risk that the user has at least one kidney disease.

19. A non-transitory computer-readable storage medium having instructions executable by one or more processors to cause the processors to perform operations comprising:

causing at least one sensor to capture sensor data corresponding to a user, the captured sensor data comprising retinal image data of the user;

receiving, from the at least one sensor, the captured sensor data;

processing the captured sensor data to determine at least one of a cardiac output of the user or a hydration status of the user;

processing the retinal image data to measure at least one of a volume of a retina of the user, a total thickness of the retina of the user, or a central subfield mean retinal thickness;

determining, based on the processed retinal image data and the at least one of the cardiac output of the user or the hydration status of the user, a risk that the user has at least one kidney disease; and transmitting a signal representing the risk that the user has at least one kidney disease to an audible or visual indicator for presenting the risk to the user.

20. The non-transitory computer-readable storage medium of claim 19, wherein:

processing the retinal image data comprises processing the retinal image data to measure the volume of the retina of the user; and determining the risk that the user has at least one kidney disease comprises determining, based on the volume of the retina of the user and the at least one of the cardiac output of the user or the hydration status of the user, the risk that the user has at least one kidney disease.

* * * * *